Sept. 11, 1956 E. S. BOERNER Plant Pat. 1,513
ROSE PLANT
Filed Nov. 2, 1955
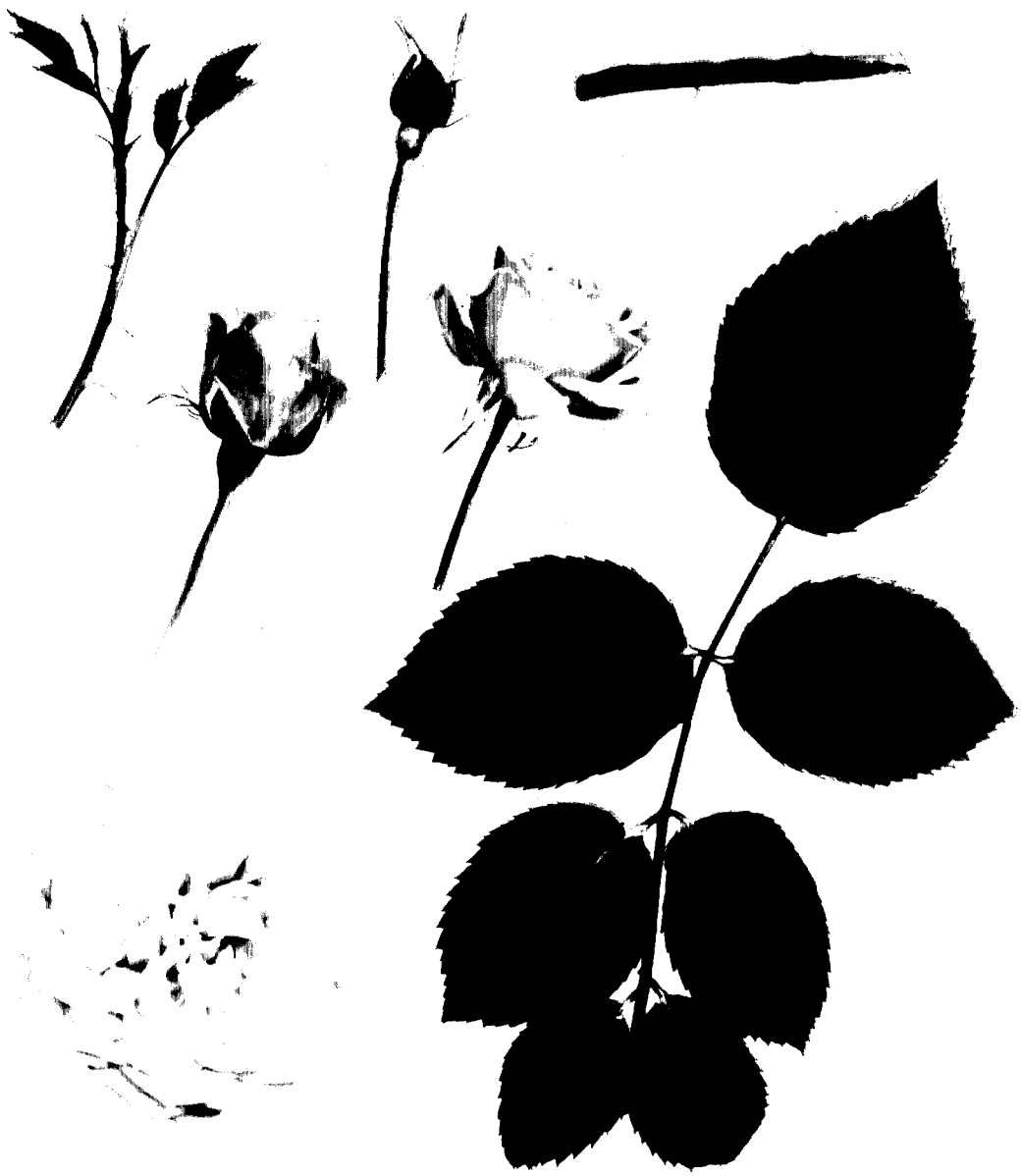
Inventor.
E. S. Boerner
By: Robb & Robb
Attorneys.

United States Patent Office

Plant Pat. 1,513
Patented Sept. 11, 1956

1,513

ROSE PLANT

Eugene S. Boerner, Newark, N. Y., assignor to Jackson & Perkins Company, Newark, N. Y., a corporation of New York Application November 2, 1955, Serial No. 544,625

1 Claim. (Cl. 47—61)

The present invention relates to a new and distinct variety of rose plant of the large-flowered polyantha class, which was originated by me by crossing an unnamed and unpatented Orange seedling of "Pinocchio" (Plant Patent No. 484) with the variety known as "Garnette" (unpatented).

The primary objective of this breeding was to produce a new Floribunda rose variety which is particularly characterized by its long-lasting flowers and their consequent improved suitability for cut flower purposes. This objective was fully achieved, along with other desirable characteristics and improvements which represent a new and distinctive combination that distinguishes the new variety from its parents, as well as from all other varieties of its class of which I am aware, as evidenced by the following predominant characteristics of the new variety:

(1) The prolificacy of flower production under greenhouse cut flower conditions, and the ease with which the variety produces such great quantities of flowers:

(2) The complete filling of the flowers with petals;

(3) The long-lasting quality of the flowers when cut, running as long as 10 days; and (4) The distinctive Begonia Rose, lightly overcast with Thulite Pink, general color tonality of the flowers.

Asexual reproduction of my new variety by budding, as performed by me at Newark, New York, and also at Pleasanton, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed Orange seedling of "Pinocchio."

*Pollen parent.*—"Garnette."

Classification:

*Botanic.*—Large-flowered polyantha.

*Commercial.*—Floribunda.

FLOWER (Observations made from specimens grown in a greenhouse at Newark, New York, in the middle of the month of August and in the early morning.)

Blooming habit: Recurrent—continuous.

Bud:

*Size.*—Small.

*Form.*—Globular; is not affected by wet or hot weather.

*Color.*—When sepals first divide—Nopal Red, Plate 1. When petals begin to unfurl—Scarlet Red, Plate 1, lightly overcast with Nopal Red, Plate 1. When half-blown: inside of petals—Dose Doree, Plate 1, lightly overcast with Deep Rose Pink, Plate 12; reverse of petals—Scarlet Red, Plate 1, lightly overcast with Begonia Rose, Plate 1.

*Sepals.*—Slightly branched; curl back when petals begin to unfurl. Color: inside—Pale Olivine, Plate 32; outside—Bice Green, Plate 17.

*Calyx.*—Color—Bice Green, Plate 17. Shape—funnel. Size—small. Aspect—smooth. Odor when rubbed—none.

*Peduncle.* — Length — medium. Strength — erect; slender. Aspect—smooth. Color—Cedar Green, Plate 6.

*Opening.*—Opens up well; is not affected by adverse weather conditions.

Bloom:

*Size.*—Medium. Average size when fully expanded —from 2¼ inches to 2½ inches.

*Flowers borne.*—Sometimes several together and sometimes in pyramidal clusters.

*Stems.*—Medium length; strong.

*Form (when first open).*—Flat. Permanence—retains its form to the end.

*Petalage.*—Very double (many petals and stamens hidden). Number of petals under normal conditions—from 75 to 80.

*Color.*—Center of flower—Rose Red, Plate 12, lightly overcast with Spinel Pink, Plate 26. Outer petals—Scarlet Red, Plate 1, lightly overcast with Begonia Rose, Plate 1. Base of petals (aiglet)—Chartreuse Yellow, Plate 31. Inside of petals—Begonia Rose, Plate 1, lightly overcast with Thulite Pink, Plate 26. Reverse of petals—Thulite Pink, Plate 26, lightly overcast with Begonia Rose, Plate 1. General tonality from a distance—Begonia Rose, Plate 1.

*Discoloration.*—General tonality at end of first day—Begonia Rose, Plate 1. Second day—Begonia Rose, Plate 1, lightly overcast with Thulite Pink, Plate 26. Third day—Begonia Rose, Plate 1, overcast with Thulite Pink, Plate 26.

Petals:

*Texture.*—Thick; is not affected by wet or hot weather.

*Appearance.*—Inside—shiny; outside—satiny.

*Form.*—Oval.

*Arrangement.* — Imbricated (regularly arranged shingle-like).

*Petaloids in center.*—Few; small.

*Persistence.*—Drop off cleanly.

*Fragrance.*—Moderate. Nature—Tea (average Hybrid Tea scent).

*Lasting quality.*—On the plant—very long. As cut flower—very long.

GENITAL ORGANS

Stamens, anthers: Small; many; mixed with petaloids. Color—Apricot Yellow, Plate 4.

Stamens, filaments (threads): Short. Color—Martius Yellow, Plate 4.

Pollen: Color—Maize Yellow, Plate 4.

Styles: Loosely separated; uneven length; medium length; thin.

Stigmas: Color—Citron Yellow, Plate 16.

Ovaries: All enclosed in calyx.

Hips: None.

Seeds: None.

PLANT

Form: Bush.
Growth: Vigorous; upright.
Foliage: Compound of 5 to 7 leaflets.
*Size.*—Medium.
*Quantity.*—Normal.
*Color.*—New foliage: upper side—Lettuce Green, Plate 5, lightly overcast with Russet, Plate 15; under side—Yellowish-Oil Green, Plate 5, lightly overcast with Russet, Plate 15. Old foliage: upper side—Varley's Green, Plate 18, lightly overcast with Hay's Russet, Plate 14; under side—Bice Green, Plate 17.
*Shape.*—Oval pointed.
*Texture.*—Upper side—leathery; under side—smooth.
*Ribs and veins.*—Ordinary.
*Edge.*—Serrated (saw-toothed).
*Serration.*—Both double and single; small.
*Leaf Stem.*—Color—Absinthe Green, Plate 31. Under side—smooth.
*Stipules.*—Medium length; slightly bearded.
Wood:
*New wood.*—Color—Bice Green, Plate 17. Bark—smooth.

*Old wood.*—Color—Forest Green, Plate 17. Bark—smooth.
Thorns:
*Thorns.*—Quantity: on main stalks from base—few; on laterals from stalk—few. Form—medium length; hooked downward; with narrow base. Color (when young)—Acajou Red, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the large-flowered polyantha class, substantially as herein shown and described, characterized particularly as to novelty by its prolific flower production under greenhouse cut flower conditions and its ease of producing such great quantities of flowers, its full flowers which are completely filled with petals, the very long-lasting quality of its flowers, and the distinctive Begonia Rose, lightly overcast with Thulite Pink, general color tonality of its flowers.

No references cited.